United States Patent [19]

Chan et al.

[11] Patent Number: 5,135,543
[45] Date of Patent: Aug. 4, 1992

[54] QUATERNIZED MONOALKYLENEDIAMINE NITROBENZENE COMPOUNDS AND THEIR USE AS DYES FOR KERATINACEOUS FIBERS

[75] Inventors: Alexander Chan, Mineola, N.Y.; Yuh-Guo Pan, Stamford, Conn.

[73] Assignee: Clairol Incorporated, New York, N.Y.

[21] Appl. No.: 762,167

[22] Filed: Sep. 19, 1991

Related U.S. Application Data

[63] Continuation of Ser. No. 459,031, Dec. 29, 1989, abandoned.

[51] Int. Cl.$^5$ ................................................ A61K 7/13
[52] U.S. Cl. ............................................... 8/405; 8/405;
8/406; 8/408; 8/415; 8/416; 8/418; 8/423;
424/70
[58] Field of Search ................... 8/405, 406, 408, 415,
8/416, 418, 423; 424/70

[56] References Cited

U.S. PATENT DOCUMENTS

| | | | |
|---|---|---|---|
| 3,904,690 | 9/1975 | Kalopissis et al. | 8/408 |
| 4,018,556 | 4/1977 | Kalopissis et al. | 8/415 |
| 4,417,896 | 11/1983 | Bugaut et al. | 8/407 |

FOREIGN PATENT DOCUMENTS

| | | |
|---|---|---|
| 0055386 | 6/1982 | European Pat. Off. |
| 0327763 | 8/1989 | European Pat. Off. |

OTHER PUBLICATIONS

Zviak, The Science of Hair Care, Marcel Dekker, Inc. 1986, pp. 235-261.

*Primary Examiner*—A. Lionel Clingman
*Assistant Examiner*—William S. Parks
*Attorney, Agent, or Firm*—Charles Zeller

[57] ABSTRACT

Quaternized monoalkylenediamine nitrobenzene compounds of general formula

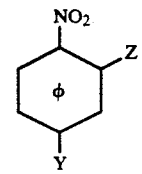

wherein one of Z or Y is the quaternized group

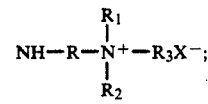

the other of Y or Z being H, alkyl hydroxyalkyl or hydroxyalkoxy when it is not said quaternized group, and the use of said compounds in the dyeing of keratinaceous fibers.

19 Claims, No Drawings

QUATERNIZED MONOALKYLENEDIAMINE NITROBENZENE COMPOUNDS AND THEIR USE AS DYES FOR KERATINACEOUS FIBERS

This application is a continuation of U.S. Ser. No. 07/459,031 filed Dec. 29, 1989, now abandoned.

FIELD OF INVENTION

This invention relates to quaternized monoalkylenediamine nitrobenzene compounds and to their use in dyeing keratinaceous fibers, particularly human hair. More particularly, it concerns compounds of the following formula and their use in dyeing human hair on the head.

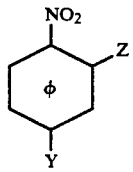

I wherein
(a) Z is selected from the group consisting of hydrogen, alkyl, hydroxyalkyl, hydroxyalkoxy and the group

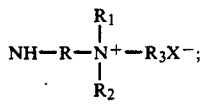

$NH-R-N^+-R_3X^-$;
with $R_1$, $R_2$ (b) Y is selected from the group consisting of H,

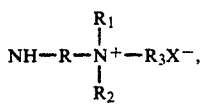

$NH-R-N^+-R_3X^-$,
with $R_1$, $R_2$ alkyl and hydroxyalkoxy;
wherein
(1) only one of Y or Z is the group

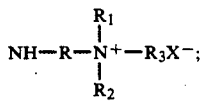

$NH-R-N^+-R_3X^-$;
with $R_1$, $R_2$ (2) R is a divalent alkylene radical;
(3) $R_1$, $R_2$ and $R_3$ are alkyl or hydroxyalkyl groups and
(4) $X^-$ is an anion.

BACKGROUND OF INVENTION

In dyeing keratinaceous fibers, particularly human hair, it is desirable that the dyed fibers have a natural appearance. This often requires blending dyes that are primarily red, blue or yellow in color in the proper portions to provide the natural looking shade. A major problem is the general lack of yellow dyes having lightfast qualities comparable to such qualities in the red and blue dyes in the shade. As a result, blended dyes containing yellow are prone to shifts in hue with normal sunlight exposure.

It has been found, unexpectedly, that the presence of the quaternary group in the compounds of formula I above shifts the light absorbancy of these compounds to the shorter wavelength when compared with the corresponding unquaternized compounds. This shift provides useful dyes having a yellower color when dyed out on keratinaceous fibers, e.g., hair or wool. It has also been found, unexpectedly, that these quaternized compounds provide dyes that have an improved lightfastness when compared with the corresponding unquaternized compounds.

PRIOR ART

U.S. Pat. Nos. 3,560,136; 3,904,690; 4,018,556 and 4,115,934 to Kalopissis et al are each directed to nitrophenylenediamine compounds said to be useful as hair dyes. The most pertinent among these is perhaps U.S. Pat. No. 4,155,934 which discloses compounds of the formula:

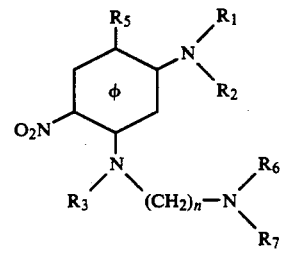

which compounds may also be quaternized.

However, the Kalopissis et al compounds of the '934 patent are structurally significantly different from the compounds of this invention. In all instances, the Kalopissis et al compounds are nitrophenylene diamines. That is, two amino groups (or substituted amino groups) are bound to the ring carbon atoms (the aromatic nucleus) of the Kalopissis et al compounds. In the compounds of the present invention only one of the amino groups is bound to a ring carbon atom These are different classes of compounds in the hair dye art and are not expected to function in the same manner, inasmuch as both amino groups present on the nucleus of the Kalopissis et al compounds contribute to the chromophoric value of the compounds. This appears quite clear from the Kalopissis et al disclosure in that both nuclear-substituted amino groups are always present and are always deemed essential. Furthermore, there is nothing in Kalopissis et al to suggest that its quaternized compounds have better lightfastness than their unquaternized compounds, as in the case with the compounds of the present invention.

U.S. Pat. No. 4,417,896 to Bugaut et al disclose compounds of general formula

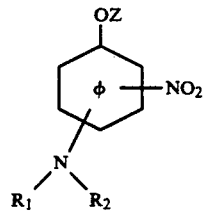

wherein Z represents a substituted lower alkyl radical and each $R_1$ and $R_2$ is hydrogen or a lower alkyl identical with or different from Z, the functional groups $-NO_2$ and $-NR_1R_2$ occupying any of the ring positions, with the stipulation that if Z is β-hydroxyethyl, —NO$_2$ is in the 4 position and the group —NR$_1$R$_2$ is in the 2 position, then either R$_1$ or R$_2$ is other than hydrogen. In this case the structure of the compound is given by the formula

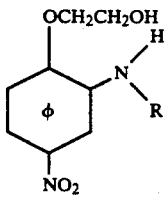

where R is not H. The compound of Example 12 in Buguat et al, which has the structure

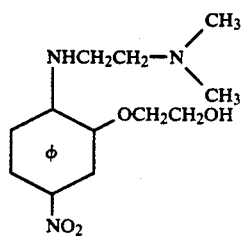

is clearly outside of the scope of the compounds of the present invention. In the case of the compounds corresponding to the unquaternized compounds of this invention, when the groups —NHCH$_2$CH$_2$N(CH$_3$)CH$_3$ and —NO$_2$ are para to each other, the position ortho to the group —NHCH$_2$CH$_2$N(CH$_3$)CH$_3$ is occupied by a hydrogen atom and not —OCH$_2$CH$_2$OH. Moreover Bugaut et al does not teach quaternizing compounds of the type shown in Example 12. The only type of quaternary compound suggested by Bugaut et al are those in which the radical carrying the quaternized group is bound to a nuclear carbon atom through an oxygen bridge, i.e.,

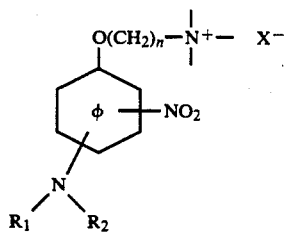

Furthermore, no precedent in the literature indicates that a quaternary ammonium center can cause a hypsochromic shift of a nitro dye molecule. The present finding that the quaternary center induces a more useful yellow color by eliminating the red hue is unexpected.

U.S. Pat. No. 3,897,496 to Crounse et al teaches quaternary ammonium compounds of the formula

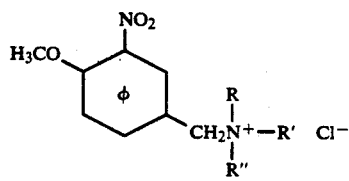

These compounds are said to be useful as germicides, fungicides and algicides. These are clearly far removed from the compounds of this invention.

West German Patent 34 25 151 discloses a direct hair dye of formula:

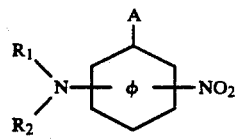

in which A is —SO$_3$H or —COOH; R$_1$ and R$_2$ are, among other things, hydrogen or (CH$_2$)$_n$X in which n is a number from 2-4, and X is —OH or —NR$_3$R$_4$, wherein R$_3$ and R$_4$ are H, alkyls of 1 to 4 carbons, hydroxyalkyls of 2 to 4 carbons or aminoalkyls having 2-4 carbons. There is no suggestion of the compounds of the present invention.

DETAILED DESCRIPTION OF INVENTION AND PREFERRED EMBODIMENT

It is a primary object of the present invention to provide a novel class of quaternary amine compounds defined by formula I above that are useful in dyeing keratinaceous fibers and particularly human hair on the head. The compounds can also be viewed as encompassing two groups of compounds defined by having the formulas:

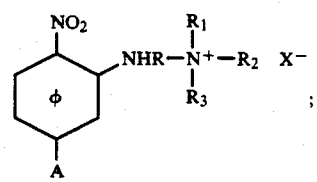

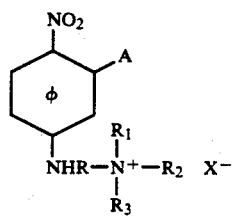

wherein R is a divalent alkylene radical typically having from 1 to about 8 carbons, which may be a straight or branched chain group, and preferably contains 2 to about 5 carbons such as ethylene, propylene, isopropylene, butylene; R$_1$, R$_2$ and R$_3$ are straight or branched chain alkyl and hydroxyalkyl radicals having up to about 6 carbons, preferably from 1 to 5 carbons, e.g., methyl, ethyl, n-propyl, isopropyl, n-butyl, t-butyl, n-pentyl, and A is H, alkyl, hydroxyalkyl and hydroxyalkoxy, the alkyl moiety, which may be straight or branch chained, having up to about 8 carbons, preferably from 1 to 5 carbons. The hydroxyalkoxy group, which usually takes the form —O—R—OH wherein R is a divalent alkylene radical as described above, may be one that contains more than one hydroxy group, e.g., —O—CH$_2$—CH(OH)—CH$_2$OH. The hydroxyalkyl radical typically will be a monovalent radical that takes the form —ROH in which R is a divalent radical as described above. This radical will also usually have up to about 5 carbon atoms in its chain.

Typical radicals of this character include —CH$_2$—CH$_2$—OH, —CH$_2$—CH(OH)—CH$_3$, —CH$_2$—CH$_2$—CH$_2$—OH, —CH$_2$—CH$_2$—CH(CH$_3$)—OH, etc. Moreover, in addition to the substituent groups designated for the aromatic nucleus in structure II and III and defined herein, the Compounds II and III may also include as ring substituents any group that does not substantially affect the chromophoric nature of the molecules.

As also indicated above, X$^-$ in formula I, II or III above is an anion. Although this is designated as a monovalent anion, it may also be a polyvalent anion such as SO$_4^-$. However, in the usual cases it will be a monovalent anion and preferably a halide. This can be illustrated by such halide ions as Cl$^-$, Br$^-$ and I$^-$. OH$^-$ is also a suitable anion.

The quaternary amine compounds of this invention may be made by reacting a compound of formula

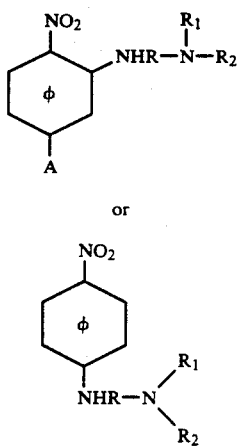

with a quaternizing agent which will ordinarily take the form of a halide of the formula R$_3$X. In this reaction A, R, R$_1$, R$_2$, R$_3$ and X have the meaning ascribed to above. More particularly, quaternization is conducted by heating an essentially equimolar mixture of amine and alkyl halide in dimethylformamide, the progress of the reaction being monitored by TLC. The desired quaternized product precipitates out after cooling to room temperature.

The quaternary ammonium compounds of this invention have special utility in dyeing keratinaceous fibers and particularly human hair. This may be used as a direct dye, i.e., as a dye that does not require an oxidizing agent in order to produce a color in the hair. However, as described in more detail below, it may also be used as a sunscreen to protect other dyes in the dye composition from fading under direct sunlight. Generally, the utilities occur concurrently so that both effects are exploited together.

When used as a direct dye it may, for example, be applied to the human head, from any of a variety of direct hair dye vehicles well known to those skilled in the art. The concentration of the dyes of this invention which will be contained in said direct hair dye vehicle may vary somewhat depending on the nature of vehicle, the presence of other hair dyes, the results desired, and the like. All that is required is that a tinctorially effective amount of the subject dyes be employed. Generally, however, the dyes herein disclosed will be present in said vehicles at a concentration in the range of from about 0.01% to about 10%, preferably from about 0.1% to about 5%, most preferably from 0.1% to 2% by weight based on total weight of the dye composition. As used herein, the term "dyeing composition" means the total dyeing composition including the dyes of this invention, other dyes if present, vehicles and adjuvants.

The vehicles employed in dyeing hair with the dyes of this invention may vary in complexity from simple solutions or dispersions that employ aqueous or aqueous alcoholic solvents to very complex systems including thickened shampoo compositions as the vehicle. Water will ordinarily constitute the major component of the dyeing compositions of this invention, but can vary widely depending on the types and quantity of adjuvants or additives contained in the composition. Thus, water may constitute as little as 10% by weight of the dyeing composition based on the total weight of the dyeing composition but more usually constitutes from about 70% to about 90% by weight on the same weight basis.

It is often advantageous to include in the dyeing compositions of the present invention an organic solvent or solvent system which helps solubilize the dyes and adjuvants contained therein. A number of organic solvents are known in the prior art that are useful for the present purposes. These include alcohols, particularly alkyl alcohols of 1–6 carbons especially ethanol and propanol; glycols of up to about 10 carbons, preferably less than 6 carbons, especially propylene glycol, butylene glycol; glycol ethers of up to about 10 carbons, especially diethyleneglycol monobutyl ether; carbitols and benzyl alcohol. When present, the solvents will constitute from about 1% to about 60%, preferably from about 10 to about 30% by weight of the dyeing composition.

The dyeing compositions of this invention may also contain other conventional adjuvants or additives commonly found in direct hair dye compositions. There include such items as surface active agents, thickening agents, alkalizing agents, chelating agents, perfumes, and the like.

The surface active agents are typically water soluble, less preferably water dispersible, and include anionic, nonionic or cationic surface active agents. Illustrative of the various types of water soluble surface active agents are: higher alkyl benzene sulfonates; alkyl naphthalene sulfonates; sulfonated esters of alcohols and polybasic acids; taurates; fatty alcohol sulfates; sulfates of branched chain or secondary alcohols; alkyl dimethylbenzyl ammonium chlorides, and the like.

Illustrative of specific surfactants are: lauryl sulfate; polyoxyethylene lauryl ester; myristyl sulfate; glyceryl monostearate; sodium salt of palmitic acid, methyl taurine; cetyl pyridinium chloride; lauryl sulfonate; myristyl sulfonate; lauric diethanolamide; polyoxyethylene stearate; stearyl dimethyl benzyl ammonium chloride; dodecyl benzene sodium sulfonate; nonyl naphthalene sodium sulfonate; dioctyl sodium sulfosuccinate; sodium N-methyl-N-oleoyl taurate; oleic acid ester of sodium isethionate; sodium dodecyl sulfate, and the like. The quantity of water soluble surface active agent employed can vary widely up to about 15%, preferably from about 0.10% to 10% by weight of the composition.

The thickening agent when employed may be one or several of those commonly used in hair dyeing, such as sodium alginate, gum arabic, cellulose derivatives such as methylcellulose or the sodium salt of carboxymethylcellulose, acrylic polymers such as polyacrylic acid sodium salt, and inorganic thickeners, e.g., bentonite. The quantity of thickening agent can vary over a wide range, typically up to about 20%, preferably from about 0.1% to 5% by weight of the composition.

The pH of the composition can vary from about 2.5 to about 11, but it is preferred that the compositions be in the alkaline range and particularly at a pH of about 7.5 to 10. Any compatible water-dispersible alkalizing agent can be incorporated in an amount suitable to give the desired pH. Illustratively, the alkalizing agent is less than about 10%, preferably from about 0.1% to about 5% by weight of the composition.

Compatible alkalizing agents are those that do not interact chemically with the dye(s) employed, will not precipitate the dye(s), and are non-toxic and non-injurious to the scalp, under the conditions of use. Preferred alkalizing agents are mono-, di- and trialkanolamines such as triethanolamine and 2-amino-2-methyl-1,3-propanediol; alkyl amines such as monoethylamine, diethylamine and dipropylamine, and heterocyclic amines such as morpholine, piperidine, 2-pipecoline and piperazine.

Any inorganic or organic acid or acid salt, which is compatible with the composition and will not introduce toxicity under its conditions of use, can also be employed for adjusting the pH of the dye composition. Illustrative of acids or acid salts are sulfuric, formic, acetic, lactic, citric or tartaric acid; ammonium sulfate, sodium dihydrogen phosphate, or potassium bisulfate.

The dyeing compositions of this invention can be prepared by the conventional methods used in the hair dyeing art. Thus, they can be prepared by dissolving or dispersing the dye in water of the desired concentration. Water miscible organic solvents can be employed to facilitate solution of the dye; in this event, the dye can be dissolved first in the solvent and then diluted with water. The dispersion of the various ingredients can also be facilitated by heating the composition.

The dyeing compositions can be applied to living human hair on the head by the conventional techniques known in the art. Illustratively they can be poured over the hair or applied with a brush, sponge, or other means of contact until the hair is properly impregnated. The time of contact of the dyeing composition with the hair is not critical and can vary over the wide range used in the hair dyeing art, such as periods of about 5 minutes to 2 hours or more, preferably from about 10 to 60 minutes. As mentioned hereinabove, the dyeing on live hair is preferably effected at temperatures below 40° C. such as those from 15° C. to 40° C., preferably at ambient room temperatures such as those of about 20° C. to 35° C.

Dyes of the present invention can also be used in combination with conventional oxidation dyes, e.g., p-phenylenediamine, α-naphthol, p-aminophenol, m-aminophenol, resorcinol and m-phenylenediamine, and their derivatives, in the presence of a conventional oxidizer such as hydrogen peroxide, to provide a range of shades on the hair. When the oxidation dye so used exhibits a degree of lightfastness lower than desired, the quaternized dyes of the present invention also function as stabilizers against shade change.

Similarly, the dyes herein disclosed can be used in combination with other conventional semipermanent dyes to produce different shades. The conventional semipermanent dyes include, e.g., o- and p-nitroanilines, nitro-p-phenylenediamines, aminoanthraquinones, aminoazobenzenes, and their derivatives.

The following examples are illustrative of a preferred form of the invention:

EXAMPLE 1

N,N,N-Trimethyl-2-(2-nitroanilino)ethanaminium Iodide

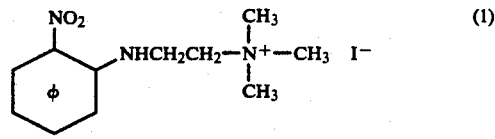

Compound (1) was prepared as indicated below:

(a) Preparation of N-(2-Dimethylamino)ethyl-2-nitroaniline.

To a stirred solution of 1-fluoro-2-nitrobenzene (7 g, 50 mmol), N,N-dimethylethylenediamine (5.2 g, 60 mmol), and potassium carbonate (7 g, 50 mmol) in 50 ml of diemethyl sulfoxide was added 0.2 g tris-(2-(2-methoxyethoxy)ethyl)amine (TDA-1). The heterogeneous mixture was heated at 90° for 2 hours. After cooling to room temperature, 100 g of crushed ice was added, the desired product was isolated by filtration in 90% yield (9.2 g, 4.5 mmol).

(b) Preparation of N,N,N-Trimethyl-2-(2-nitroanilino)ethanaminium iodide.

A solution of N-(2-dimethylamino)ethyl-2-nitroaniline (1.0 g, 5 mmol) and methyl iodide (0.9 g, 6 mmol) in 10 ml of dimethylformamide was heated at 90°. The progress of reaction was monitored by tlc until the disappearance of starting material. After cooling to room temperature, the quaternary ammonium salt was isolated in 95% yield (1.7 g, 4.5 mmol). Its melting point was 191°–3° C.

EXAMPLE 2

N,N-Dimethyl-N-(2-hydroxyethyl)-2-(2-nitroanilino)ethanaminium Bromide

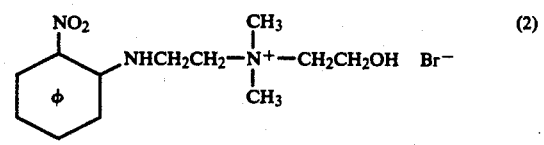

Compound (2) was prepared as indicated below: N-(2-Dimethylamino)ethyl-2-nitroaniline 1.25 q, 10 mmol) was heated at 100° with 2-bromoethanol (6 g, 50 mmol) until the disappearance of starting material (monitored by tlc). Excess of 2-bromoethanol was removed in vacuo to give the quaternized salt in quantitative yield. Its melting point was 105°–8° C.

EXAMPLE 3

N,N,N-Trimethyl-2-(5-β-hydroxyethoxy-2-nitroanilino)ethanaminium Iodide

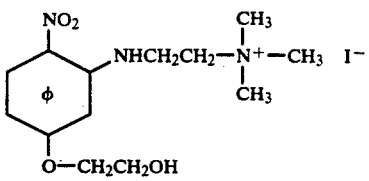

Compound (3) was prepared as follows:

To a stirred solution of 2,4-difluoronitrobenzene (3.2 g, 20 mmol), N,N-dimethylethylenediamine (1.76 g, 20 mmol), and potassium carbonate (2.8 g, 20 mmol) was heated at 80° for 2 hours in dimethyl sulfoxide with catalytic amount of TDA-1. Another equivalent of potassium carbonate and 5 eq of ethylene glycol was added and heating was continue for another hour. After aqueous workup, an orange oil was obtained which was quaternized in dimethylformamide to give the desired product in 70% yield (5.8 g, 14 mmol). Its melting point was 238°–40° C.

EXAMPLE 4

N,N,N-Trimethyl-2-(5-methyl-2-nitroanilino)ethanaminium Iodide

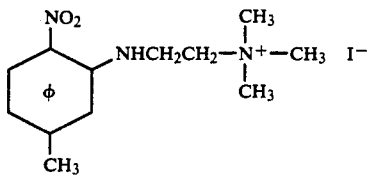

Compound (4) was prepared as follows:

To a stirred solution of 3,4-dinitrotoluene (3.64 g, 20 mmol) and N,N-dimethylethylenediamine (1.76 g, 20 mmol) was heated at 80° C. in dimethyl sulfoxide and catalytic amount of TDA-1 for 2 hours. N,N-Dimethyl-2-(5-methyl-2-nitroanilino)ethanamine was isolated in 80% yield (3.6 g, 16 mmol) after aqueous work-up. Quaternization was achieved in quantitative yield with methyl iodide and dimethylformamide. Its melting point was 225°–7° C.

EXAMPLE 5

N,N,N-Trimethyl-4-(2-nitroanilino)ethanaminium Iodide

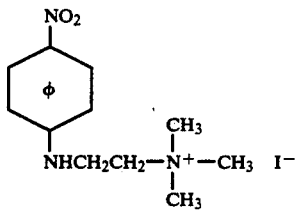

Compound (5) was prepared as set forth below:

The synthesis of the compound (5) was the same as in Example 1, except 1-fluoro-4-nitrobenzene (7 g, 50 mmol) was employed. Its melting point was 119°–203° C. (decomposed).

Dyeing compositions of the present invention are illustrated in the following examples:

EXAMPLE 6

The following dyeing composition containing the Compound (1) of Example 1 was made by admixing the various constituents:

| Constituents | Concentration (wt %) |
| --- | --- |
| Compound (1) | 0.3 |
| Aminomethyl propanol | 1.0 |
| Hydroxymethyl cellulose | 1.4 |
| PEG-50 Tallow amide | 1.5 |
| Lauramide DEA | 1.5 |
| Oleic acid | 2.0 |
| Diethyleneglycol monoethyl ether | 5.0 |
| Water | q.s. 100% |

This mixture was applied to blended gray hair for about 30 minutes at room temperature, rinsed and washed by shampooing. A bright orange-yellow color was obtained on hair.

EXAMPLE 7

The Compound (3) of Example 3 was used in the following composition:

| Constituents | Concentration (wt %) |
| --- | --- |
| Compound (3) | 0.3 |
| Ethanol (95% aq. sol'n) | 33.0 |
| Diethanolamine | to pH 9.5 |
| Water | q.s. 100% |

This composition was used to treat bleached hair by applying it to the hair for 30 minutes at room temperature. An intense yellow color was obtained.

EXAMPLE 8

This example illustrates the ability of the quaternized dyes of the present invention to protect conventional dyes from the effect of sunlight. Solution A below is a conventional oxidative dye lotion to be used in an oxidative dyeing procedure. Solution B further contains 0.3% Compound (3).

| | Concentration (wt %) | |
| --- | --- | --- |
| Constituents | A | B |
| p-phenylenediamine HCl | 0.23 | 0.23 |
| α-Naphthol | 0.18 | 0.18 |
| Compound (3) | — | 0.30 |
| Ethanol (95% aq. sol'n) | 37 | 37 |
| Water | q.s. 100% | q.s. 100% |

8 ml Solution A was mixed with 5 ml of a 6% hydrogen peroxide solution, pH being adjusted to 9.6 with concentrated ammonium hydroxide. The resulting solution was applied to dye blended gray hair for 30 minutes. A violet color was obtained. The hair was then rinsed and shampooed. Solution B was similarly applied to blended gray hair to obtain a golden brown shade.

Both tresses were subjected to a test for lightfastness using an Atlas color Fad-ometer instrument, Type FDA-RC. The before and after color values were measured and recorded as changes in the Hunter Tristimulus values L, a and b. The test was conducted for 5 hours. The total shade change, designated as x, is calculated from the expression $x = [(\Delta a)^2 + (\Delta b)^2]^{\frac{1}{2}}$. In this case, when x=0 there is no change in the shade, i.e., the lower the number, the less the change in shade. The swatch treated with Solution A displayed a total change of 3 units, while the swatch treated with Solution B exhibited a change of only 1.2 units.

EXAMPLE 9

This example illustrates the utility of the quaternized dyes of the present invention when used in combination with conventional semipermanent dyes. As shown below, the use of the subject quaternized dyes not only provides the ability to modify the shades normally obtained, but also protects the semipermanent dyes from conventional fading occasioned by light.

| Constituent | Concentration (wt. %) | | | |
|---|---|---|---|---|
| | A | B | C | D |
| Semipermanent Dye #1[2] | 1.47 | 2.94 | 0.87 | 1.0 |
| Semipermanent Dye #2[2] | — | — | 1.47 | — |
| Compound (1)[3] | — | — | — | 1.47 |
| Monoethanolamine | ←q.s. to pH 10→ | | | |
| Ethanol (95% Aq. Sol'n) | 33.0 | 33.0 | 33.0 | 33.0 |
| Water | ←q.s. 100%→ | | | |

[1] N-2-hydroxyethyl-o-2-hydroxyethoxy-p-nitroaniline
[2] N-2-dimethylaminoethyl-o-nitroaniline
[3] N,N,N-trimethyl-2-(2-nitroanilino)ethanaminium iodide Solution D is within the scope of the present invention, while Solutions A-C are not. Four gray hair tresses were prepared by treating each of the swatches with one of the Solutions A-D for 30 minutes at room temperature. Solution D dyed the gray hair bright yellow, while Solution C provided a weaker yellow color. Both Solutions A and B produced a greenish-yellow color on the gray hair, but the intensity was stronger in the tress treated with Solution B due to a higher concentration of semipermanent dye #1.

All of the tresses were exposed to direct sunlight for about 25 hours, the tress treated with Solution D undergoing the least shade change, as indicated below.

| Solution | Total Unit Change in Shade (x)* |
|---|---|
| A | 4.9 |
| B | 5.0 |
| C | 4.1 |
| D | 1.0 |

*See text at Example 8 for discussion of Total Unit Shade Change value, x.

To demonstrate that the quaternization of compounds of formulas IV and V above shifts the light absorbance of the dye to a shorter wavelength than that recorded for the corresponding nonquaternized compounds, the following experiments were carried out:

EXPERIMENT A

A series of dye compositions were prepared each containing a different dye recited in Table I. With reference to Compound I, the structures of the dyes contained in respect of compositions of the series mentioned above are given in Table I below. As will be noted compound 1', 3', 4' and 5' are nonquaternized versions of compounds 1, 2, 3, 4 and 5.

TABLE 1

| Compound | Y | Z |
|---|---|---|
| 1 | H | NH(CH$_2$)$_2$N$^+$(CH$_3$)$_3$ I$^-$ |
| 1' | H | NH(CH$_2$)$_2$N(CH$_3$)$_2$ |
| 2 | H | NH(CH$_2$)$_2$N$^+$(CH$_3$)$_2$CH$_2$CH$_2$ OH Br$^-$ |
| 3 | OCH$_2$CH$_2$OH | NH(CH$_2$)$_2$N$^+$(CH$_3$)$_3$ I$^-$ |
| 3' | OCH$_2$CH$_2$OH | NH(CH$_2$)$_2$N(CH$_3$)$_2$ |
| 4 | CH$_3$ | NH(CH$_2$)$_2$N$^+$(CH$_3$)$_3$ I$^-$ |
| 4' | CH$_3$ | NH(CH$_2$)$_2$N(CH$_3$)$_2$ |
| 5 | NH(CH$_2$)$_2$N$^+$(CH$_3$)$_3$ I$^-$ | H |
| 5' | NH(CH$_2$)$_2$N(CH$_3$)$_2$ | H |

The compositions were as follows:

| Ingredient | Compositions | | |
|---|---|---|---|
| | For Dye Pairs 1,1' and 3,3' | For Dye 2 and Dye Pairs 4,4' | For Dye Pair 5,5' |
| Dye of Table I | 30 mg | 30 mg | 40 mg |
| Ethanol (95% Aq. Soln.) | 4 ml | 3.5 ml | 4 ml |
| Water | 6 ml | 6.5 ml | 6 ml |
| Monoethanolamine | ←q.s. to pH 9.5→ | | |

Each of said dye compositions containing each of the nine dyes identified in Table I was used to dye wool fibers samples. The composition was applied to the wool fibers for about 30 minutes at room temperature, followed by a water rinse.

The maximum absorption wavelength of the respective nitro dyes mentioned above in isopropyl alcohol was measured as well as the color values (i.e., the Hunter Tristimulus L, a and b values) on wool cloth obtained from said dye compositions containing the respective nitro dyes. The results of these tests are summarized in Table II below:

TABLE II

Maximum Absorption Wavelength of the Nitro Compounds in Isopropyl alcohol and the Color on Wool Cloth

| Compound* | i-PrOH λmax (nm) | Initial Values | | |
|---|---|---|---|---|
| | | L | a | b |
| 1 | 405 | 68.4 | −6.5 | 42.9 |
| 1' | 423 | 60.7 | 7.3 | 40.0 |
| 2 | 408 | 66.2 | −6.8 | 40.0 |
| 3 | 396 | 70.0 | −14.4 | 37.2 |
| 3' | 410 | 68.9 | −13.1 | 41.0 |
| 4 | 405 | 67.9 | −9.7 | 38.6 |
| 4' | 414 | 61.0 | 8.5 | 40.3 |
| 5 | 367 | 72.4 | −15.9 | 36.3 |
| 5' | 380 | 70.1 | −15.3 | 43.2 |

*1', 3', 4' and 5' are the nonquaternized analogues of 1, 2, 3, 4 and 5.

An examination of the wavelength data (column 2) shows that the presence of the quaternary center in the nitro dye molecule shifts the light absorbance maximum (λmax) of the dye to a shorter wavelength. Compare 1 and 2 with 1', 3 with 3', 4 with 4' and 5 with 5'. No shift was found in the absorption spectrum if a foreign quaternary ammonium salt was added to the solution of one of the nitro dyes, i.e., 1'-5'. This demonstrates a significant interaction between the quaternary centers and the dye chromophore since the λmax's of this class of dyes has shifted from blue to yellow approximately 15 nm when compared with the nonquaternized analogues.

An examination of the Hunter Tristimulus values indicates that on wool, the color is more yellow when the quaternized form of the dye is employed and the red hue is suppressed. Compare particularly the "a" values for compounds with and without the quaternary center. In the case of the Hunter Tristimulus "a" values, the lower the number, the greener the color and, conversely, the higher the Hunter Tristimulus "a" value, the redder the color. Hence, when the red hue in the dye out is suppressed, the yellow becomes more dominant.

EXPERIMENT B

The photostability of the dyes of Table I, i.e., the lightfastness of dyeings on wool and bleached hair, was measured. The stability was represented by the changes in final Hunter Tristimulus values of the fiber after it wa exposed to light from its initial tristimulus values. The dyeing procedure employed was described above with respect to Experiment A, and the lightfastness test was performed in an Atlas Color Fad-ometer equipped with a carbon arc lamp. A piece of wool cloth (2.5 cm × 10 cm) or a swatch of bleached hair (about 2 g) was treated with the solution for 30 minutes. The treated sample was then rinsed, and subjected to illumination after it was dry.

The color changes resulting from these tests were measured and recorded as changes in the tristimulus values L, a and b. The total shade change, designated as x, is calculated from the expression $x=[(\Delta a)^2+(\Delta b)^2]^{\frac{1}{2}}$. In this case, when x=0 there is no change in the shade, i.e., the lower the number, the less the change in shade.

The results of these tests are summarized in Table III.

TABLE III

Comparison of Photostability of Nitro-dyes with and without a quaternary Ammonium Center

| Compound* | $\Delta L$ | $\Delta a$ | $\Delta b$ | x** |
|---|---|---|---|---|
| 1 | −0.5 | −1.1 | 1.9 | 2.2 |
| 1' | −0.4 | −2.2 | −2.7 | 3.3 |
| 3 | −3.6 | 6.4 | −7.4 | 9.8 |
| 3' | −6.7 | 8.0 | −7.4 | 10.9 |
| 4 | −2.1 | −0.2 | −1.6 | 1.6 |
| 4' | −2.2 | −2.5 | −2.1 | 3.3 |
| 5 | −2.9 | 3.6 | 2.3 | 4.3 |
| 5' | −4.7 | 7.1 | −1.2 | 7.2 |

*The study was done on wool for 1, 1', 3, 3', 5 and 5'; and on bleached hair for 4 and 4'.
**$x = [(\Delta a)^2 + (\Delta b)^2]^{\frac{1}{2}}$ An examination of the last column of Table III shows that in each case the quaternized compound designated by the number without the prime showed less change in shade when exposed to light in accordance with the protocol than the analogous nonquaternized compound.

What is claimed is:

1. A hair dyeing composition useful as a direct dye on hair comprising a hair dye carrier, adjuvants selected from the group consisting essentially of surface active agents, thickening agents, alkalizing agents, chelating agents and perfumes, and a tinctorially effective amount of a quaternized monoalkylenediamine nitrobenzene compound of formula:

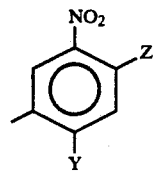

wherein:
(a) Z is a radical selected from the group consisting of H, alkyl, hydroxyalkyl, hydroxyalkoxy, wherein the akyl moieties are from 1 to 8 carbon atoms, and

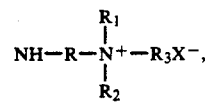

and
(b) Y is a radical selected from the group consisting of H, alkyl, hydroxyalkyl, hydroxyalkoxy, wherein the alkyl moieties are of from 1 to 8 carbon atoms, and

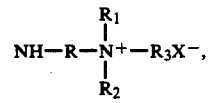

wherein
(1) one only of Y or Z is the radical

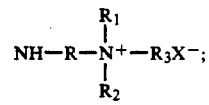

(2) R is a divalent alkylene radical of from 1 to 8 carbon atoms,
(3) $R_1$, $R_2$, and $R_3$ are alkyl or hydroxyalkyl of from 1 to 6 carbon atoms, and
(4) X is an anion.

2. The hair dyeing composition of claim 1 wherein R is a lower divalent alkylene radical having 2 to 5 carbons, and $R_1$, $R_2$ and $R_3$ are lower alkyl or lower hydroxyalkyl radicals having 1 to 5 carbons.

3. The hair dyeing composition of claim 1 wherein the compound of formula (I) is from about 0.01 to about 10% by weight of the composition.

4. The hair dyeing composition of claim 2 wherein the compound of formula (I) is from about 0.01 to about 5% by weight of the composition.

5. The hair dyeing composition of claim 2 wherein X is a halide, $OH^-$ or $SO_4^=$.

6. The hair dyeing composition of claim 4 wherein Z is

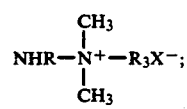

Y is a radical selected from the group consisting of H, $R_1$ and —O—ROH, and X is selected from halide, $OH^-$ and $SO_4^=$.

7. The hair dyeing composition of claim 6 wherein Z is

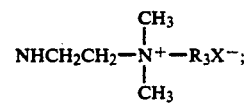

$R_3$ is $CH_3$, $CH_2CH_3$ or $CH_2CH_2OH$; Y is H, $CH_3$, $CH_2CH_3$, $CH_2CH_2OR$ or $OCH_2CH_2OH$, and X is a halide.

8. The hair dyeing composition of claim 7 wherein X is I or Br, Y is H or $CH_3$ and $R_3$ is $CH_3$ or $CH_2CH_2OH$.

9. The hair dyeing composition of claim 7 wherein X is I or Br, Y is $OCH_2CH_2OH$, and $R_3$ is $CH_3$ or $CH_2CH_2OH$.

10. A hair dyeing composition of claim 4 wherein Z is a radial selected from the group consisting of H, $R_1$ and $-O-ROH$, Y is

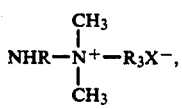

and $X^-$ is a halide.

11. The hair dyeing composition of claim 10 wherein is

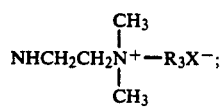

$R_3$ is $CH_3$, $CH_2CH_3$ or $CH_2CH_2OH$; Z is H, $CH_3$, $CH_2CH_3$, $CH_2CH_2OH$ or $OCH_2CH_2OH$, and X is a halide.

12. The hair dyeing composition of claim 11 wherein X is I or Br, Z is H or $CH_3$ and $R_3$ is $CH_3$ or $CH_2CH_2OH$.

13. The hair dyeing composition of claim 11 wherein X is I or Br, Z is $CH_2CH_2OH$ and $R_3$ is $CH_3$ or $CHCH_2OH$.

14. A hair dye composition comprising a hair dye carrier having incorporated therein a tinctorially effective amount of a hair dye subject to being deleteriously affected by sunlight and selected from the group consisting of p-phenylenediamine, α-naphthol, p-aminophenol, m-aminophenol, resorcinol, m-phenylenediamine, and derivatives thereof and o- and p-nitroanilines, nitro-p-phenylenediamines, aminoanthraquinones, and derivatives thereof, said composition also containing a sun protective amount of from about 0.01 to about 10% of a quaternized monoalkylenediamine nitrobenzene compound of general formula

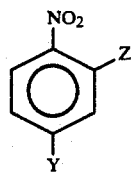

wherein
(a) Z is a radical selected from the group consisting of H, alkyl, hydroxyalkyl, hydroxyalkyloxy, wherein the alkyl moieties are of from 1 to 8 carbon atoms, and

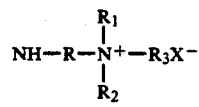

and
(b) Y is a radical selected from the group consisting of H, alkyl, hydroxyalkyl, hydroxyalkoxy, wherein the alkyl moieties are of 1 to 8 carbon atoms, and

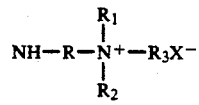

wherein
(1) one only of Y or Z is the radical

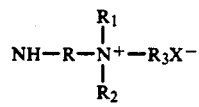

(2) R is a divalent alkylene radical of from 1 to 8 carbon atoms,
(3) $R_1$, $R_2$ and $R_3$ are alkyl or hydroxyalkyl, of from 1 to 6 carbon atoms,
(4) X is an anion,
whereby said dye is significantly protected against deterioration by sunlight.

15. The hair dyeing composition of claim 14 wherein the compound of formula (I) is from about 0.01 to about 2% by weight of the composition.

16. The hair dye composition of claim 14 wherein the deleteriously affected hair dye is an oxidative dye.

17. The hair dye composition of claim 14 wherein the deleteriously affected hair dye is a semipermanent dye.

18. A process for dyeing hair which comprises applying to said hair a composition of claim 1 in sufficient amount to effectively color said hair.

19. A process for dyeing hair which comprises applying to said hair a composition of claim 14 in sufficient amount to effectively color said hair.

* * * * *